United States Patent
Aguirre et al.

(10) Patent No.: US 8,740,876 B2
(45) Date of Patent: Jun. 3, 2014

(54) DEVICE FOR EXTERNAL PERCUTANEOUS CONNECTIONS

(75) Inventors: Andres F. Aguirre, Chicago, IL (US); Richard W. Ducharme, Winston-Salem, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 380 days.

(21) Appl. No.: 13/104,355

(22) Filed: May 10, 2011

(65) Prior Publication Data
US 2011/0288534 A1 Nov. 24, 2011

Related U.S. Application Data

(60) Provisional application No. 61/332,911, filed on May 10, 2010.

(51) Int. Cl.
*A61M 25/00* (2006.01)
*A61M 5/32* (2006.01)

(52) U.S. Cl.
USPC .......................... 604/535; 604/533; 604/174

(58) Field of Classification Search
CPC ........... A61B 2017/00477; A61B 2017/00876; A61J 15/0015; A61J 15/0049; A61J 15/0057; A61M 2039/0255; A61M 2039/0261; A61M 2039/027; A61M 2039/0276; A61M 2039/0282; A61M 2039/0297; A61M 39/0247; A61M 39/10
USPC .......................... 604/533, 535, 174, 175, 178
See application file for complete search history.

(56) References Cited

U.S. PATENT DOCUMENTS

| | | |
|---|---|---|
| 3,908,646 A | 9/1975 | Ansari |
| 4,393,873 A | 7/1983 | Nawash et al. |
| 4,666,433 A | 5/1987 | Parks |
| 4,790,809 A | 12/1988 | Kuntz |
| 4,863,438 A | 9/1989 | Gauderer et al. |
| 4,865,030 A | 9/1989 | Polyak |
| 4,957,479 A | 9/1990 | Roemer |
| 4,989,299 A | 2/1991 | Morita |
| 5,176,626 A | 1/1993 | Soehendra |
| 5,334,208 A | 8/1994 | Soehendra et al. |
| 5,336,203 A | 8/1994 | Goldhardt et al. |
| 5,466,242 A | 11/1995 | Mori |

(Continued)

FOREIGN PATENT DOCUMENTS

| | | |
|---|---|---|
| EP | 1 600 121 A1 | 11/2005 |
| WO | WO 03/103541 A1 | 12/2003 |
| WO | WO 2011/143174 A1 | 11/2011 |

OTHER PUBLICATIONS

Brochure entitled "Tiger Tube" Self-Advancing Nasal Jejunal Feeding Tube—Cook Interventional Critical Care Products—Cook Incorporated 2004.

(Continued)

*Primary Examiner* — Kami A Bosworth
*Assistant Examiner* — Imani Hayman
(74) *Attorney, Agent, or Firm* — Brinks Gilson & Lione

(57) ABSTRACT

The present invention provides devices for creating an external percutaneous fluidic connections. In one embodiment, the device includes a first tube defining a longitudinal axis, and a first bolster supporting the first tube, a second tube, and a second bolster supporting the second tube. The first and second bolsters are magnetically attractable, and promote airflow to the skin.

23 Claims, 5 Drawing Sheets

(56) References Cited

U.S. PATENT DOCUMENTS

| | | |
|---|---|---|
| 5,514,176 A | 5/1996 | Bosley, Jr. |
| 5,556,385 A | 9/1996 | Andersen |
| 5,643,277 A | 7/1997 | Soehendra et al. |
| 5,647,843 A | 7/1997 | Mesrobian et al. |
| 5,720,734 A | 2/1998 | Copenhaver et al. |
| RE35,849 E | 7/1998 | Soehendra |
| 5,800,517 A | 9/1998 | Anderson et al. |
| 5,876,450 A | 3/1999 | Johlin, Jr. |
| 6,231,549 B1 | 5/2001 | Noecker et al. |
| 6,258,098 B1 | 7/2001 | Taylor et al. |
| 6,652,569 B1 | 11/2003 | Taylor et al. |
| 6,997,909 B2 | 2/2006 | Goldberg |
| 7,582,072 B2 | 9/2009 | McMichael |
| 2004/0193115 A1 | 9/2004 | Itrich et al. |
| 2007/0016131 A1 | 1/2007 | Munger et al. |
| 2007/0156117 A1 | 7/2007 | Adams et al. |
| 2008/0264413 A1 | 10/2008 | Doherty et al. |
| 2009/0318854 A1* | 12/2009 | Bailey .............................. 604/27 |

OTHER PUBLICATIONS

Wiley Encyclopedia of Biomedical Engineering, entitled "STENTS" (10 pages) by C. Lally et al. Copyright 2006 John Wiley & Sons, Inc.—10 pages.

International Search Report and Written Opinion (PCT/US08/73081) dated Oct. 27, 2008 in related application.

International Search Report and Written Opinion (PCT/US2011/035865) dated Jul. 27, 2011 in related application.

Article entitled "Novel NIST Connector Uses Magnets for Leak-Free Microfluidic Devices"—J. Atencia, et al., Published online Nov. 16, 2009 (2 pages).

Brochure entitled "Kimberly-Clark* MIC-KEY* Low-Profile Gastrostomy Feeding Tube" (4 pages) Copyright 2006.

Brochure entitled "MIC-KEY* Care Guide", Copyright 2005 (pp. 1-18).

* cited by examiner

US 8,740,876 B2

DEVICE FOR EXTERNAL PERCUTANEOUS CONNECTIONS

CROSS-REFERENCE

This application claims the benefit of U.S. Provisional Application Ser. No. 61/332,911 filed on May 10, 2010, entitled "DEVICE FOR EXTERNAL PERCUTANEOUS CONNECTIONS," the entire contents of which are incorporated herein by reference.

FIELD OF THE INVENTION

The present invention relates generally to external percutaneous connections to an internal organ or bodily lumen.

BACKGROUND OF THE INVENTION

Many types of external percutaneous connections form to provide a patient or medical staff with access to an internal organ or bodily lumen. For example, semi-permanent connections are made through the skin for placement of IV lines, catheters, dialysis lines, colostomy bags and the like. Percutaneous endoscopic gastrostomy tubes, commonly known as PEG tubes, are used as a means of feeding when a person is unable to eat. PEG tubes are typically inserted through a small incision in the abdomen into the stomach. These tubes may be form placed, or large support bolsters having adhesive pad are used to anchor the tube in place such that a portion extends into the stomach, and an opposing portion extends out of the stomach and through the skin for external access.

BRIEF SUMMARY OF THE INVENTION

The present invention provides devices for creating an external percutaneous fluidic connections. In one embodiment, the device includes a first tube defining a longitudinal axis, and a first bolster supporting the first tube. The first bolster has a first outer ring, a first inner hub, and a first plurality of spokes interconnecting the first inner hub and the first outer ring. The first plurality of spokes define a first plurality of openings therebetween, and the first inner hub is attached to the first tube. The first bolster is at least partially constructed of a ferromagnetic material. The device further includes a second tube, and a second bolster supporting the second tube. The second bolster has a second outer ring, a second inner hub, and a second plurality of spokes interconnecting the second inner hub and the second outer ring. The second plurality of spokes define a second plurality of openings therebetween, and the second inner hub is attached to the second tube. The second bolster includes a magnet creating a magnetic field attractive to the ferromagnetic material of the first bolster.

According to more detailed aspects, the first plurality of openings are in communication with the second plurality of openings to allow air to pass therethrough. The magnet is annular shaped and includes a proximal side opposite a distal side. The second outer ring is connected to the distal side of the magnet. Preferably, the second outer ring, the second inner hub and the second plurality of spokes are constructed of a polymer having ferromagnetic particles embedded therein, whereby the magnetic flux of the magnet flows through the ferromagnetic particles. Optionally, the second bolster may also include a third outer ring, a third inner hub, and a third plurality of spokes linking the third inner hub to the third outer ring. The third plurality of spokes define a third plurality of openings therebetween. The third inner hub is attached to the second tube, and the third outer ring attached to the proximal side of the magnet. The first, second and third plurality of openings are in communication with each other to allow air to pass through to the skin surrounding the stoma where the first tube enters the body.

According to still further detailed aspects, the first bolster is preferably constructed of a polymer having ferromagnetic particles embedded therein, and most preferably an elastomer such as Silicone®. The magnet of the second bolster may be formed by a plurality of magnetized particles embedded within the second bolster. A distal end of the second tube projects distally beyond the second bolster, and is sized to be received within the first tube. The first tube includes a proximal end and a valve adjacent the proximal end, and wherein the distal end of the second tube opens the valve when positioned within the first tube.

DETAILED DESCRIPTION OF THE INVENTION

The terms "proximal" and "distal" as used herein are intended to have a reference point relative to the user. Specifically, throughout the specification, the terms "distal" and "distally" shall denote a position, direction, or orientation that is generally away from the user and towards a target site, and the terms "proximal" and "proximally" shall denote a position, direction, or orientation that is generally towards the user and away from a target site. Thus, "proximal" and "distal" directions, portions of a device, or bodily regions, may depend on the point of entry for the procedure (e.g., percutaneously or laparoscopically or endoscopically).

Figure 1:
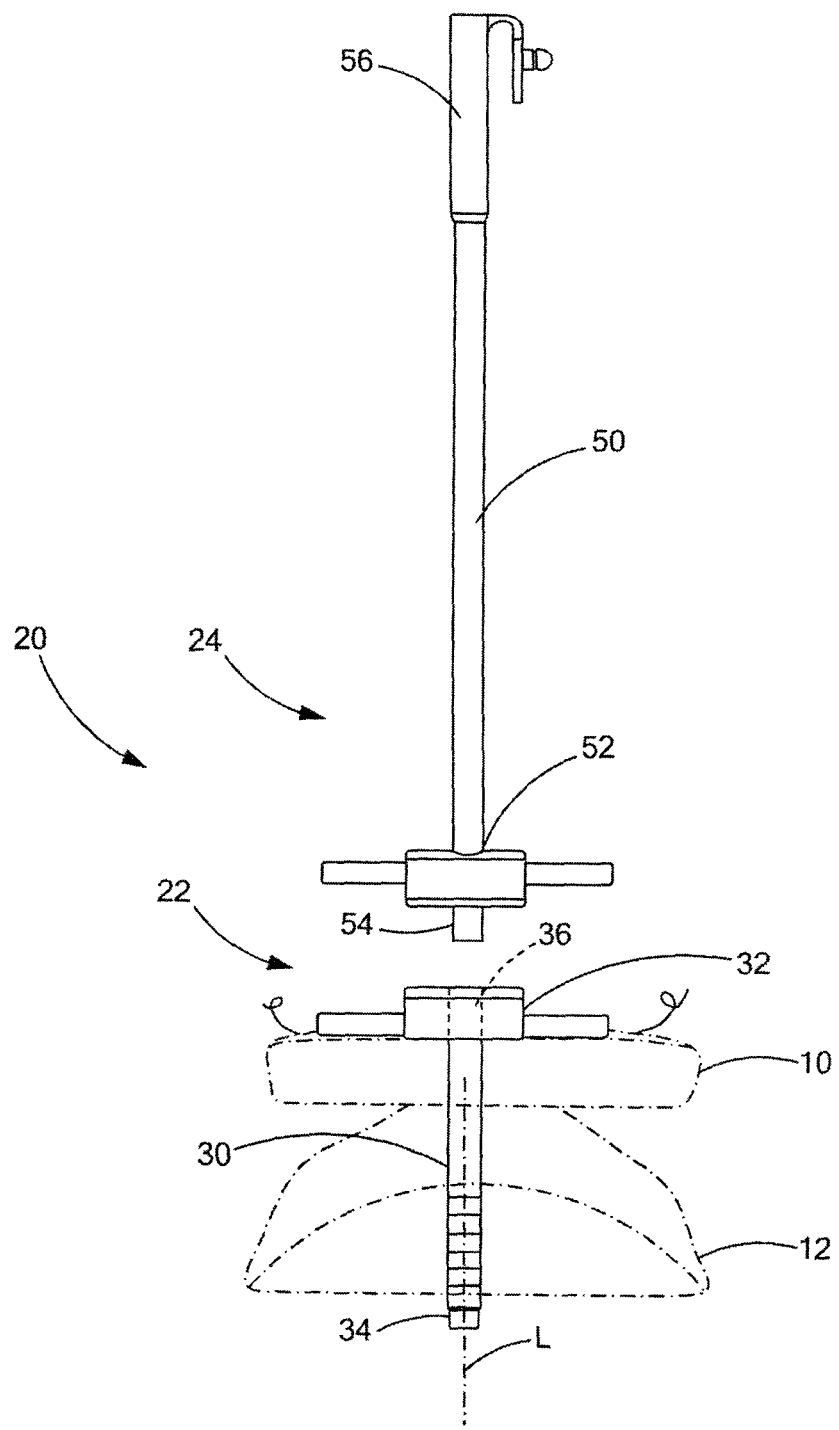
FIG. 1 is a plan view of a device for creating an external percutaneous fluidic connection.

Turning now to the figures, FIG. 1 depicts a front view of a device 20 for creating an external percutaneous fluidic connection. Generally, the device 20 has been depicted as a gastrostomy feeding device (e.g., a PEG tube), however it will be recognized by those skilled in the art that the device 20 can be applied to form many different external percutaneous connections, including IV lines, internally placed catheters, dialysis lines, colostomy bags and the like. The device 20 generally includes an internal component 22 and an external component 24. The internal component may be selectively connected to the external component 24 to create a fluidic connection to an internal organ or bodily lumen, depicted in FIG. 1 as the stomach 12.

The internal component 22 includes a first tube 30 which is placed through an opening in the abdominal wall 10 and corresponding opening in the stomach wall 12 (i.e. a stoma). A distal portion 34 of the tube 30 is positioned inside of the stomach 12, while a proximal end 36 of the tube 30 is accessible from outside of the body. The first tube 30 is supported by a first bolster 32 which also is positioned along the exterior of the stomach wall 10.

The external component 24 includes a second tube 50 supported by a second bolster 52. The second bolster 52 selectively mates with the first bolster 32 linking the first tube 30 with the second tube 50 to create an external percutaneous fluidic connection. The distal end 54 of the second tube 50 extends through the bolster 52 and is positioned for fluidic connection to the proximal end 36 of the first tube 30. The proximal end 56 of the second tube 50 remains accessible to the patient and medical professional, for example for the introduction of food or medication. Accordingly, the proximal end 56 is adapted for connection to a feeding pump, syringe or the like.

Figure 2:
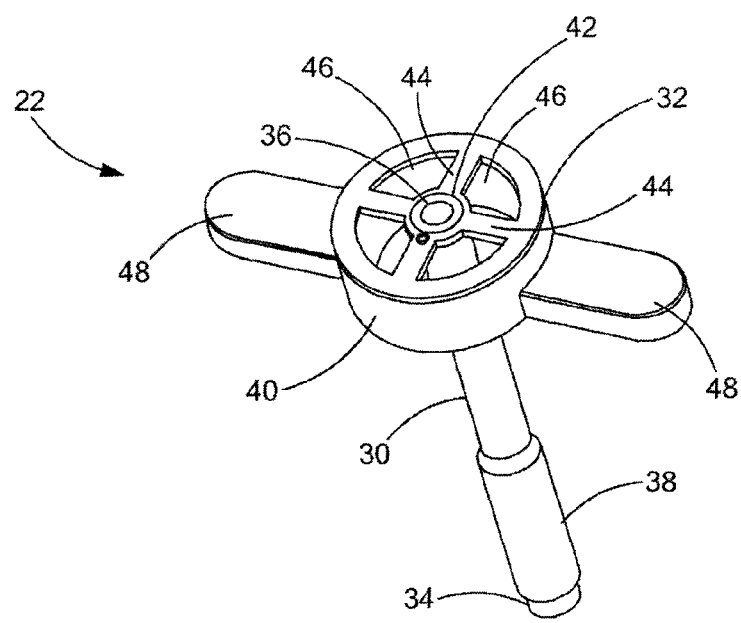
FIG. 2 is a perspective view of an internal component forming a portion of the device depicted in FIG. 1.

Turning now to FIG. 2, the internal component 22 is shown in greater detail. The first tube 30 includes an extendable member 38 located adjacent the distal end 34 of the first tube 30. The expandable element 38 is preferably an inflatable balloon, although those skilled in the art will literally recognize that the anchoring member 38 may comprise many structures including expandable wings, correctional threads and the like. The first bolster 32 generally includes a first outer ring 40, a first inner hub 42, and a first plurality of spokes 44 interconnecting the first inner hub 42 and the first outer ring 40. In the depicted embodiment, the first plurality of spokes 44 include four spokes, and define a first plurality of opening 46 between the spokes 44. More particularly, the plurality of spaces 46 are defined between the spokes 44, the inner hub 42 and the outer ring 40. Two diametrically opposed tabs 48 are shown as attached to the outer ring 40 to provide a structure that is easy to grasp for manipulation of the internal component 22.

Figure 3:
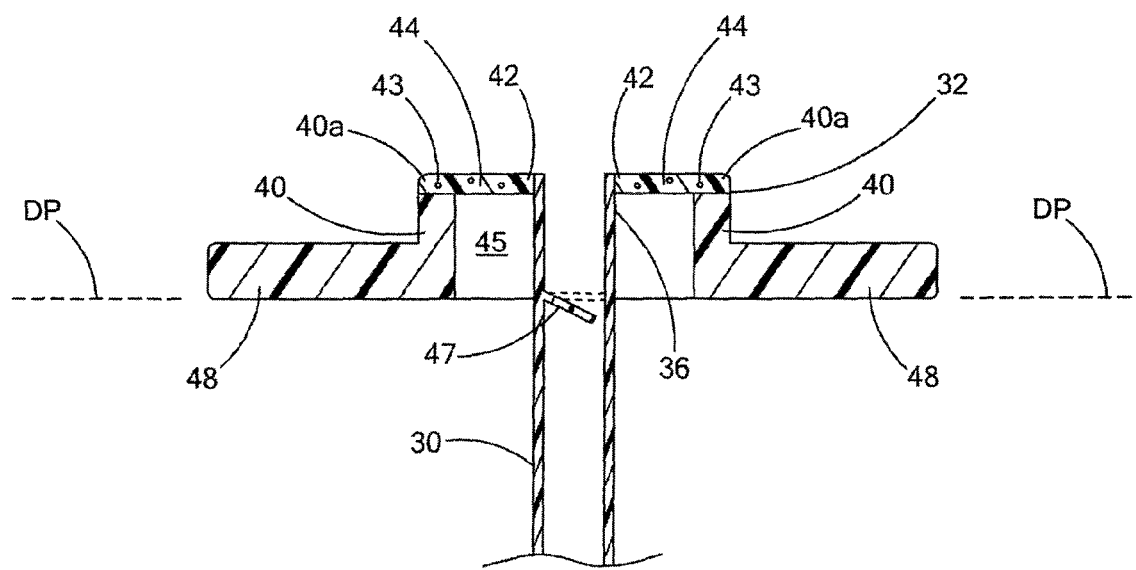
FIG. 3 is a cross-sectional view of the internal component depicted in FIG. 2.

As best seen in FIG. 3, this embodiment of the first bolster 32 has been shown as formed by two elements. The outer ring 40 has been shown formed unitarily and integrally with the tab 48, while the first inner hub 42, first plurality of spokes 44 have been shown unitarily and integrally formed together and with their own outer ring component 40a. This auxiliary outer ring 40a has a radial thickness corresponding to the thickness of the first outer ring 40, and the auxiliary outer ring 40a may be attached to the first outer ring 40 using adhesives, plastic welding or other well known bonding techniques. However, it will be recognized that the outer ring 40 and/or tab 48 may be unitarily and integrally formed with the first inner hub 42 and first plurality of spokes 44, and the entire bolster 32 may be impregnated with ferromagnetic particles 43. Accordingly, the first inner hub 42, the first plurality of spokes 44 and the auxiliary outer ring 40a may be formed of a polymer material that is embedded with ferromagnetic particles 43 (for attraction to magnet 59, discussed further hereinbelow). Alternatively, any of the components of the first bolster 32, such as the first outer ring 40, the first inner hub 42, or the first spokes 44, may be formed entirely of a ferromagnetic material, such as steel. Preferably, the polymer material of the first bolster 32 is an elastomer, and most preferably is formed of silicone or Santoprene™ to create a soft bolster. The first bolster 32 can also be coated with a material such as Parylene™ to reduce friction with the skin of the abdominal wall 10.

As best seen in FIG. 3, the proximal end 36 of the first tube 30 is connected to the first inner hub 42 of the first bolster 32, preferably using a friction fit, adhesives, plastic welding, or other known bonding techniques. Notably, distal sides of the first inner hub 42 and the first plurality of spokes 44 are spaced proximally away from the abdominal wall 10. Stated another way, the first outer ring 40 includes a distal side defining a distal plane DP which is structured to rest against the abdominal wall 10, and the distal sides of the first inner hub 42 and first spokes 44 are spaced away from the distal plane DP. According, the large interior space 45 defined by the first outer ring 40 is in communication with the first plurality of openings 46 between the spokes 44, thereby allowing airflow to the abdominal wall 10 and stoma, or other skin area of the patient.

It can also be seen in FIG. 3 that the proximal end 36 of the first tube 30 includes a valve, depicted in the figure as a simple flap valve 47. When the valve 47 is pressed upon by the distal end 54 of the second tube 50, the flap valve 47 moves to an open position as depicted in FIG. 3. When there is no force on the flat valve 47, it returns to a closed position indicated by the dotted lines in FIG. 3, thereby preventing some of the contents from inadvertently exiting via the first tube 30.

Figure 4:
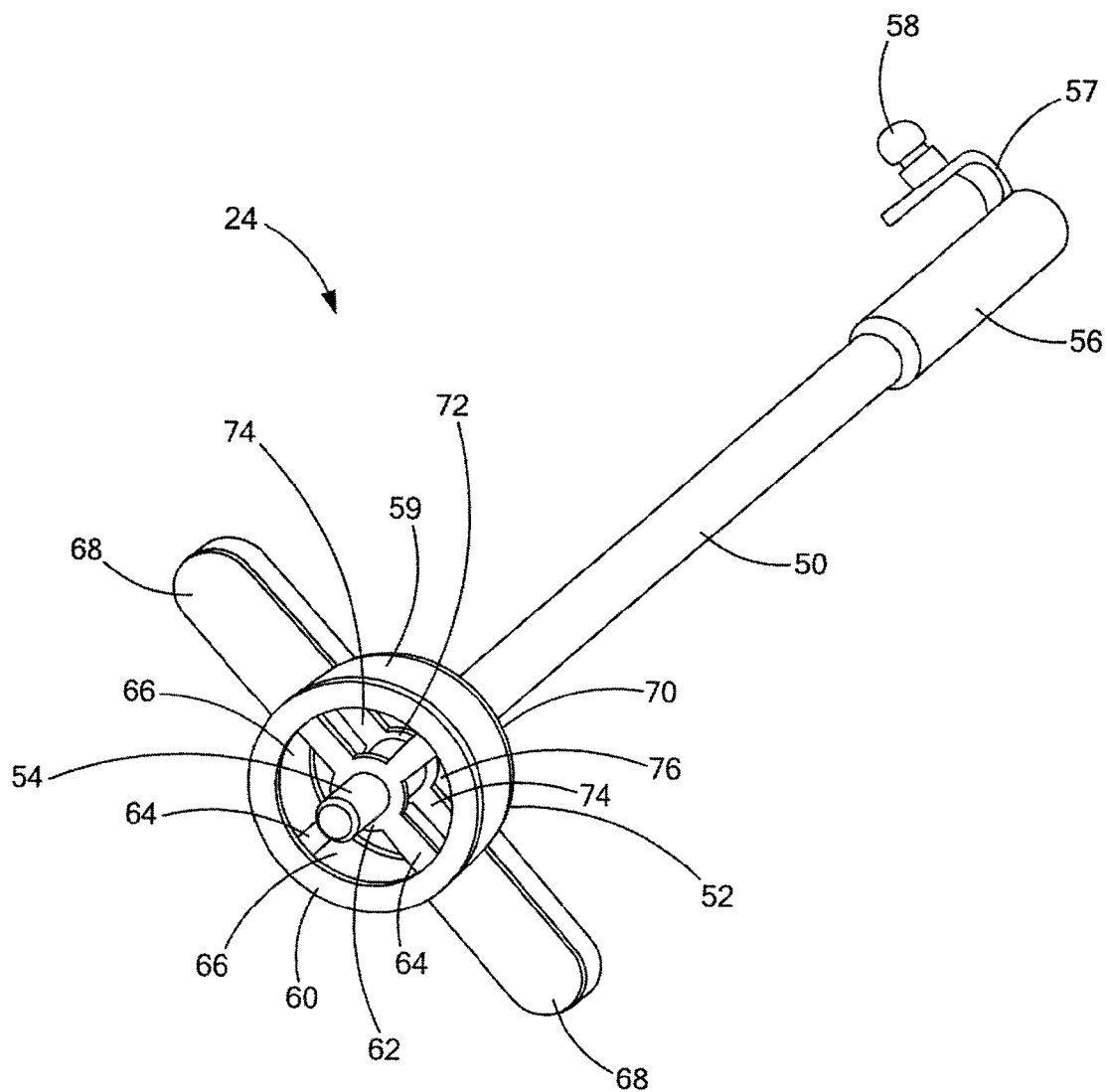
FIG. 4 is a perspective view of an external component forming a portion of the device depicted in FIG. 1.

Turning now to FIG. 4, the external component 24 is shown in greater detail, and generally comprises the second tube 50 and second bolster 52. The distal end 54 of the second tube 50 projects through the bolster 52 for entrance into the proximal end 36 of the first tube 30 and engagement with the valve 47 as described above. When connected, the tubes 30, 50 are generally aligned and concentrically arranged around the longitudinal axis L. The proximal end 56 of the second tube 50 generally includes a flap 57 having a stopper 58 which can be used to seal off the proximal end 56 of the second tube 50, or opened up as shown for connection to a feeding pump, syringe or other medical device. Likewise, the second tube 50 may be partially or wholly replaced by another tubular member such as a colostomy bag or the like.

The second bolster 52, much like the first bolster 32, includes a second outer ring 60, a second inner hub 62, and a second plurality of spokes 64 interconnecting the second inner hub 62 and second outer ring 60. The second plurality of spokes 64 define a second plurality of openings 66 therebetween. The second inner hub 62 is attached to the proximal end 54 of the second tube 50 to provide support thereto.

Notably, the second bolster 52 includes a magnet 59. As depicted in FIG. 4, the magnet 59 is preferably an annular shaped magnet having a radial thickness corresponding to the thickness of the second outer ring 60. This thickness dimension also preferably corresponds to a thickness of the first outer ring 40 to promote airflow when the internal and external components 22, 24 are connected. The annular magnet 59 is attached to the second outer ring 60 through use of adhesives or other bonding techniques known in the art. The magnet 59 creates a magnetic field that is attractive to the ferromagnetic material in the first bolster 32, thereby providing a selective connection between the first and second bolsters 32, 52. Thus, when the second bolster 52 and its magnet 59 are placed sufficiently close to the first bolster 32, the external component 24 will connect to the internal component 22 such that the second tube 50 is placed in fluidic connection with the first tube 30 as previously described. To help focus the magnetic flux of the magnet 59, the second outer ring 60, second inner hub 62 and second plurality of spokes 64 may be formed similarly to those of the first bolster 32, namely of a polymer (and preferably an elastomer) having ferromagnetic particles embedded therein. It will also be recognized that the particles may also be magnetized rather than simply being ferromagnetic.

To further support the second tube 50 and magnet 59, the second bolster 52 may further include a third outer ring 70, a third inner hub 72 and a third plurality of spokes 74 interconnecting the third inner hub 72 and third outer ring 70. The third inner hub 72 is connected to the second tube 50, preferably using a friction fit, adhesives or plastic bonding techniques. The magnet 59 includes a distal side and a proximal side, and the second outer ring 60 is attached to the distal side while the third outer ring 70 is attached to the proximal side of the magnet 59, again using adhesives or other known bonding techniques. A pair of diametrically opposed tabs 68 may be connected to any of the magnet 59, second outer ring 60 or third outer ring 70 to provide a secure gripping surface for the patient or medical professional.

Figure 5:
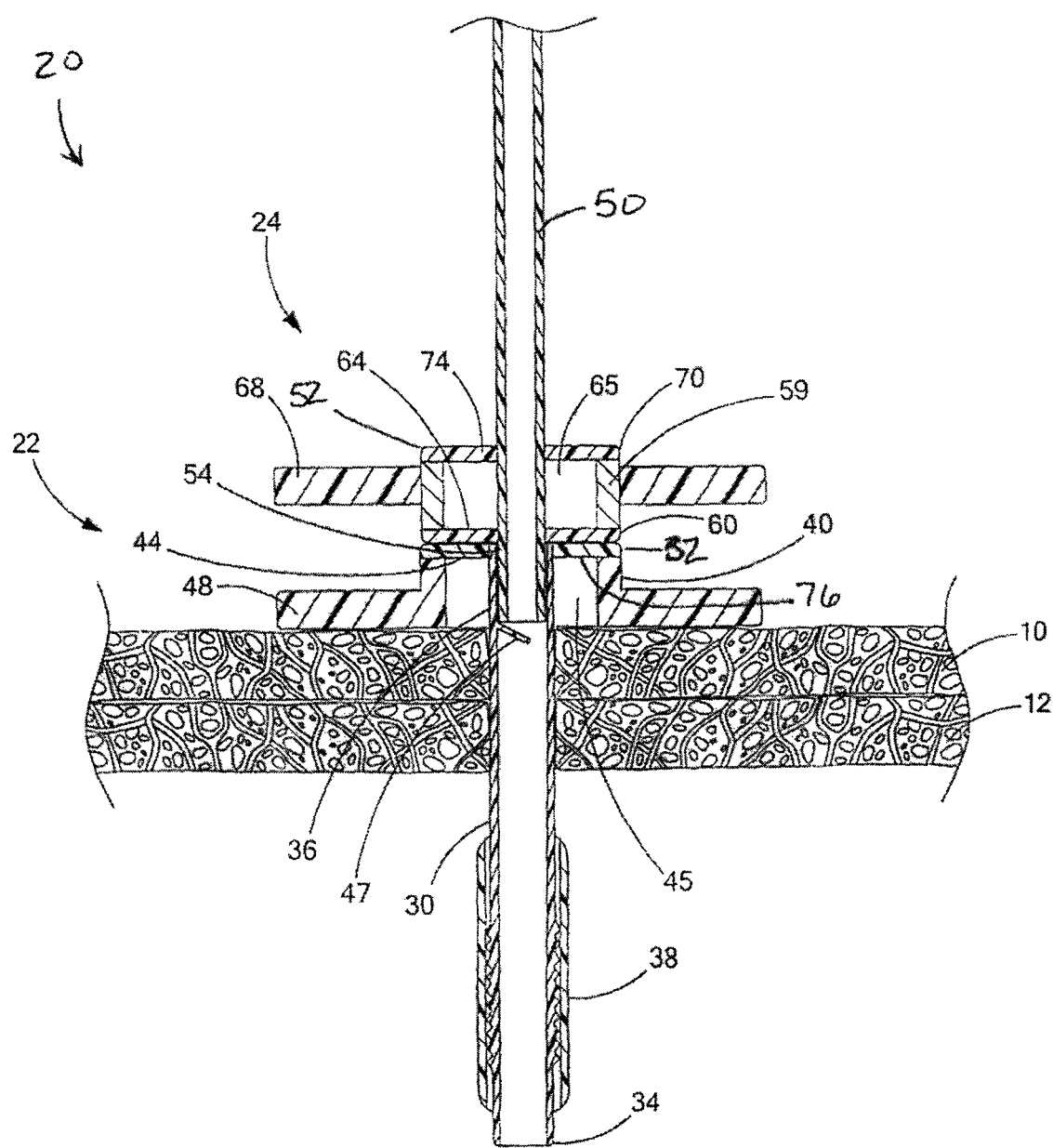
FIG. 5 is a cross-sectional view of the device depicted in FIG. 1 and shown in a state of connection.

As shown in FIG. 5, when the second bolster 52 is placed sufficiently close to the first bolster 32, the magnet 59 of the second bolster 52 will be attracted to the ferromagnetic material 43 (FIG. 3) of the first bolster 32. Due to the distal end 54 of the second tube 50 projecting beyond the second bolster 52, the magnet 59 can be placed closest to the second bolster 32 only when the distal end 54 projects into the proximal end 36 of the first tube 30. In this connected state depicted in FIG. 5, the distal end 54 of the second tube 50 projects into the tube 30 such that it opens up the flat valve 47. In this manner, an external percutaneous fluidic connection is made between the external component 24 and the internal component 22, thereby allowing materials to flow from the exterior of the patient through the second tube 50 and first tube 30 and into the stomach 12 or other visceral or lumen of the patient.

Figure 6:
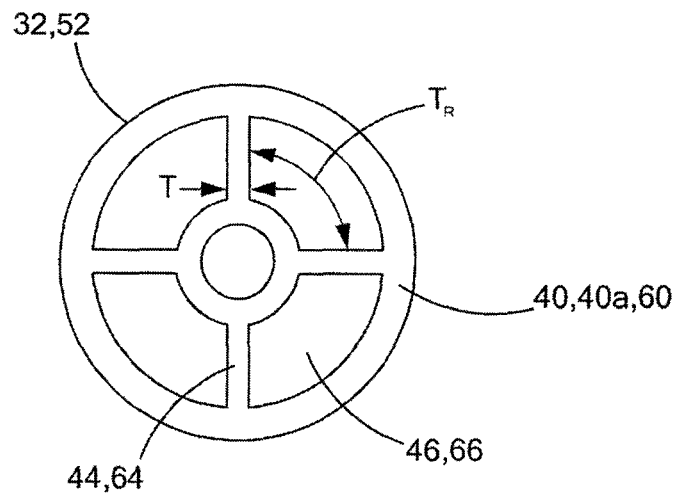
FIG. 6 is a plan view of first and second bolsters forming portions of the device depicted in FIG. 1.

Notably, in a connected state shown in FIG. 5, the device 20 provides significant airflow through to the stoma and skin of the abdominal wall 10. In particular, air may flow through the third plurality of openings 76, through the interior space 65 defined by the magnet 59, through the second plurality of openings 66 and the first plurality of openings 46, and through the interior space 45 of the first bolster 32. Airflow is ensured through the large openings 46, 66, 76. As shown in FIG. 6, the plurality of openings 46, 66, 76 have an arc length or radial thickness $T_r$ that is greater than a thickness T of the plurality of spokes 44, 64, 74, preferably at least two times greater, and most preferably at least three times greater. Accordingly, even when the spokes 44, 64, 74 aren't perfectly aligned in a circumferential direction, and thus when the openings 46, 66, 76 are not perfectly aligned, there is still a fluidic connection between the openings 46, 66 such that air can flow from the second interior space 65 of the second bolster 52 to the first interior space 45 of the first bolster 32.

Figure 7:
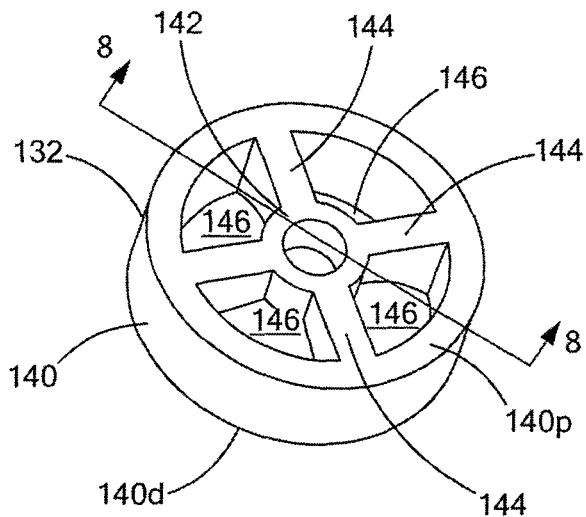
FIG. 7 is a perspective view of an alternate embodiment of a bolster forming a portion of the device depicted in FIG. 1.
Figure 8:
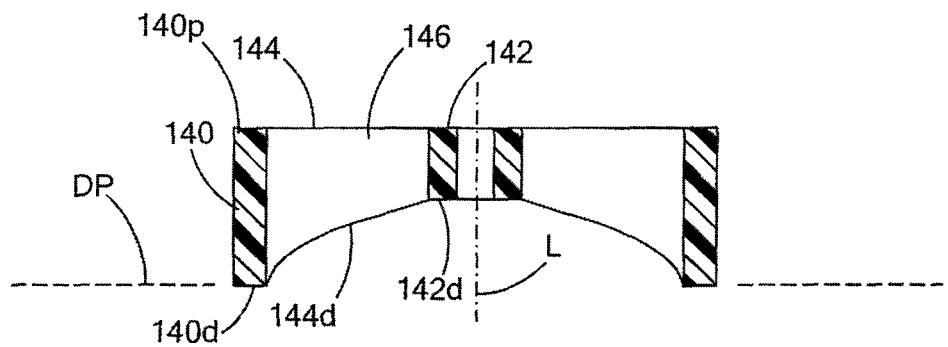
FIG. 8 is a cross-sectional view of the bolster depicted in FIG. 6.

Turning now to FIGS. 7 and 8, another alternate embodiment of the first bolster 132 is depicted. As with the previous embodiments, the first bolster 132 generally includes an outer ring 140, an inner hub 142, and a plurality of spokes 144 interconnecting the inner hub 142 and outer ring 140. A plurality of openings 146 are defined between the spokes 144. As best seen in FIG. 8, the outer ring 140 includes a proximal side 140p and a distal side 140d, the distal side 140d defining a distal plane DP. The distal plane DP is generally perpendicular to the longitudinal axis L ("generally" as used herein includes within 5%). Here again the inner hub 142 includes a distal side 142d that is spaced away from the distal plane, and likewise the plurality of spokes 144 include a distal side 144d that is also spaced away from the distal plane DP. Notably, the distal surface 144d of the spokes 144 is curved such that a vertical height of these spokes 144 decreases as based in from the outer ring 140 to the inner hub 142. It can also be seen that this embodiment of the bolster 132 may be formed as a single, unitarily and integrally formed piece, preferably of a polymer impregnated with ferromagnetic materials.

Many other variations of the device 20 are also possible. For example, the magnet 59 of the second bolster 52 need not be formed as an annular shaped magnet, but may rather be a series of discrete magnets arranged in an annular shape. Likewise, the magnet 59 may be a plastic material having a series of space to part magnets embedded therein and extending circumferentially around the first tube 50. Further, the second bolster 52 could be replaced with a design similar to that depicted in FIGS. 7 and 8, and formed from a polymer material that is embedded with magnetized particles. That is, magnetizable particles may be embedded in the polymer material, which are then magnetized to provide a magnetic flux that is attractive to the first bolster 32. Similarly the third outer ring 70, third inner hub 72 and third spokes 74 and the design of FIGS. 4 and 5 are optional. As previously noted, the second tube 50 may also be partially and wholly replaced with other devices such as colostomy bags or the like.

Similarly, to facilitate the connective state shown in FIG. 5, the diameter of second bolster 52 may be a size larger than the diameter of the first bolster 32 such that the bolsters 52, 32 nest within each other to ensure the first and second tubes 30, 50 are aligned with the longitudinal axis L. The first and second bolsters 32, 34, and in particular their mating surfaces (i.e. the proximal surface of the first bolster 32 and the distal surface of the second bolster 52) may have other mating features such as tabs and detents, pins and holes or the like which facilitate alignment of the first and second tubes 30, 50, as well as alignment of the spokes 44, 64.

The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

The invention claimed is:

1. A device for creating an external percutaneous fluidic connection, the device comprising:
    a first tube defining a longitudinal axis;
    a first bolster supporting the first tube, the first bolster having a first outer ring, a first inner hub, and a first plurality of spokes interconnecting the first inner hub and the first outer ring, the first plurality of spokes defining a first plurality of openings therebetween, the first inner hub attached to the first tube, the first hub defining a first aperture receiving the first tube, and wherein the first bolster is at least partially constructed of a ferromagnetic material;
    a second tube; and
    a second bolster supporting the second tube, the second bolster having a second outer ring, a second inner hub, and a second plurality of spokes interconnecting the second inner hub and the second outer ring, the second plurality of spokes defining a second plurality of openings therebetween, the second inner hub attached to the second tube, the second hub defining a second aperture receiving the second tube, and wherein the second bolster includes a magnet creating a magnetic field attractive to the ferromagnetic material of the first bolster.

2. The device of claim 1, wherein the first plurality of openings are in communication with the second plurality of openings to allow air to pass therethrough when the first and second bolsters are magnetically connected.

3. The device of claim 1, wherein the magnet is annular shaped and includes a proximal side and a distal side opposite the proximal side.

4. The device of claim 3, wherein the second outer ring is connected to the distal side of the magnet.

5. The device of claim 4, wherein the second outer ring, the second inner hub and the second plurality of spokes are constructed of a polymer having ferromagnetic particles embedded therein, the magnet having a magnetic flux flowing through the ferromagnetic particles.

6. The device of claim 4, wherein the second bolster includes a third outer ring, a third inner hub, and a third plurality of spokes linking the third inner hub to the magnet, the third plurality of spokes defining a third plurality of openings therebetween, the third inner hub attached to the second tube, the third outer ring attached to the proximal side of the magnet.

7. The device of claim 6, wherein the first plurality of openings are in communication with the second plurality of openings, and the second plurality of openings are in communication with the third plurality of openings to allow air to pass through the first, second and third plurality of openings.

8. The device of claim 1, wherein the first bolster is constructed of a polymer having ferromagnetic particles embedded therein.

9. The device of claim 1, wherein the magnet is formed by a plurality of magnetized particles embedded within the second bolster.

10. The device of claim 1, wherein the first outer ring includes a distal side defining a distal plane generally perpendicular to the longitudinal axis, and wherein the first plurality of spokes are spaced away from the distal plane.

11. The device of claim 10, wherein the first plurality of spokes include a distal surface that is curved relative to the distal plane.

12. The device of claim 10, wherein the first inner hub includes a distal side spaced away from the distal plane.

13. The device of claim 1, wherein the first plurality of spokes includes four spokes.

14. The device of claim 13, wherein the second plurality of spokes includes four spokes.

15. The device of claim 1, wherein the first outer ring includes a pair of tabs projecting outwardly therefrom to facilitate grasping the first bolster.

16. The device of claim 1, wherein the second outer ring includes a pair of tabs projecting outwardly therefrom to facilitate grasping the second bolster.

17. A device for creating an external percutaneous fluidic connection, the device comprising:
a first tube defining a longitudinal axis;
a first bolster supporting the first tube, the first bolster having a first outer ring, a first inner hub, and a first plurality of spokes interconnecting the first inner hub and the first outer ring, the first plurality of spokes defining a first plurality of openings therebetween, the first inner hub attached to the first tube, and wherein the first bolster is at least partially constructed of a ferromagnetic material;
a second tube; and
a second bolster supporting the second tube, the second bolster having a second outer ring, a second inner hub, and a second plurality of spokes interconnecting the second inner hub and the second outer ring, the second plurality of spokes defining a second plurality of openings therebetween, the second inner hub attached to the second tube, wherein a distal end of the second tube projects distally beyond the second bolster, and wherein the distal end is sized to be received within the first tube, and wherein the second bolster includes a magnet creating a magnetic field attractive to the ferromagnetic material of the first bolster.

18. The device of claim 17, wherein the first tube includes a proximal end and a valve adjacent the proximal end, and wherein the distal end of the second tube opens the valve when positioned within the first tube.

19. The device of claim 17, wherein the first plurality of openings are in communication with the second plurality of openings to allow air to pass therethrough when the first and second bolsters are magnetically connected.

20. The device of claim 17, wherein the first outer ring includes a distal side defining a distal plane generally perpendicular to the longitudinal axis, and wherein the first plurality of spokes are spaced away from the distal plane.

21. A device for creating an external percutaneous fluidic connection, the device comprising:
a first tube defining a longitudinal axis;
a first bolster supporting the first tube, the first bolster having a first outer ring, a first inner hub, and a first plurality of spokes interconnecting the first inner hub and the first outer ring, the first plurality of spokes defining a first plurality of openings therebetween, the first inner hub attached to the first tube, and wherein the first bolster is at least partially constructed of a ferromagnetic material;
a second tube; and
a second bolster supporting the second tube, the second bolster having a second outer ring, a second inner hub, and a second plurality of spokes interconnecting the second inner hub and the second outer ring, the second plurality of spokes defining a second plurality of openings therebetween, the second inner hub attached to the second tube, wherein the first and second tubes pass at least partially through the first and second inner hubs, respectively, and wherein the second bolster includes a magnet creating a magnetic field attractive to the ferromagnetic material of the first bolster.

22. The device of claim 21, wherein the first plurality of openings are in communication with the second plurality of openings to allow air to pass therethrough when the first and second bolsters are magnetically connected.

23. The device of claim 21, wherein the first outer ring includes a distal side defining a distal plane generally perpendicular to the longitudinal axis, and wherein the first plurality of spokes are spaced away from the distal plane.

* * * * *